United States Patent [19]

Rohrmann et al.

[11] Patent Number: 5,391,790

[45] Date of Patent: Feb. 21, 1995

[54] PROCESS FOR THE PREPARATION OF BRIDGED, CHIRAL METALLOCENE CATALYSTS OF THE BISINDENYL TYPE

[75] Inventors: Jürgen Rohrmann, Kelkheim; Frank Küber, Oberursel, both of Germany

[73] Assignee: Hoechst Aktiengesellschaft, Frankfurt am Main, Germany

[21] Appl. No.: 76,991

[22] Filed: Jun. 15, 1993

[30] Foreign Application Priority Data

Jun. 13, 1992 [EP] European Pat. Off. ............ 92109988

[51] Int. Cl.⁶ .......................... C07F 7/02; C07F 7/22; C07F 7/30
[52] U.S. Cl. ........................................ 556/28; 556/9; 556/87; 556/89; 556/95; 556/104; 556/478; 585/27
[58] Field of Search ................... 556/9, 28, 87, 89, 95, 556/104, 478; 585/27

[56] References Cited

U.S. PATENT DOCUMENTS 5,103,030  4/1992  Rohrmann et al. .................. 556/12

FOREIGN PATENT DOCUMENTS 0426643  5/1991  European Pat. Off. .

*Primary Examiner*—José G. Dees
*Assistant Examiner*—Porfirio Nazario-Gonzalez
*Attorney, Agent, or Firm*—John M. Genova

[57] ABSTRACT

A process for the preparation of a compound of the formula III

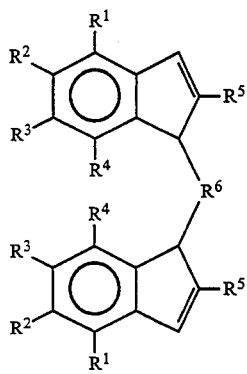

comprising, deprotonating a solution or suspension of an indene of the formula I

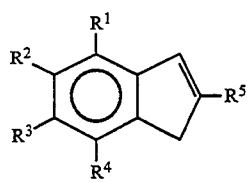

in a solvent or solvent mixture containing a base to give a suspension of a metallated product of the compound of formula I, adding to the suspension of the metallated product a compound of the formula II $$X-R^6-X \qquad (II)$$

and reacting the suspension of the metallated product and compound of the formula II.

5 Claims, No Drawings

PROCESS FOR THE PREPARATION OF BRIDGED, CHIRAL METALLOCENE CATALYSTS OF THE BISINDENYL TYPE

The present invention relates to a process for the preparation of bridged metallocenes which can very advantageously be employed as catalyst components in the preparation of isotactic polypropylene, polypropylene waxes and copolymers of various olefins, such as, for example, ethylene, propylene and norbornene.

Bridged metallocenes in combination with aluminoxanes are highly active, stereospecific catalysts for the preparation of polyolefins. In particular, the corresponding bridged, chiral zirconium derivatives are of considerable importance as highly active catalysts in the polymerization of olefins (cf. EP-A 129 368; EP 0 321 852). The chiral zirconocenes can be employed as racemates. It is merely necessary to remove quantitatively the meso forms produced during their preparation since these do not polymerize stereospecifically. By varying the ligand system, for example by substitution, the catalyst properties can be modified in a targeted manner. This makes it possible to modify the polymer yield, the molecular weight, the tacticity or melting point of the polymer to the desired extent (German patent 41 28 238.8; New J. Chem. 14 (1990) 499; EP-A 351 392).

Bridged bisindenylzirconocenes containing unsubstituted or substituted indenyl ligands and silicon or ethylene bridges are of particular importance for use as catalysts on a large industrial scale.

Numerous syntheses of bridged ligand systems of this type and the corresponding bridged, chiral bisindenyl metallocenes are known (U.S. Pat. No. 4,985,576; DE 40 35 883; J. Am. Chem. Soc. 73 (1951) 5135; Angew. Chem. Int. Ed. Engl. 28 (1989) 1511; J. Organomet. Chem. 342 (1988) 21; U.S. Pat. No. 5,017,714).

According to the prior art, the silicon- or ethylene-bridged bisindenyl ligand systems are prepared by deprotonation of the corresponding indenes using strong bases such as butyllithium, alkali metal hydrides or elemental potassium, and subsequent reaction with bisalkyldichlorosilanes or dibromoalkyl compounds. Ethylenebridged ligand systems can also be synthesized by reaction of the corresponding indenyl Grignard compounds with dibromoethane. The solvents used in all reactions are ethereal solvents, generally diethyl ether or tetrahydrofuran, since the starting materials and the alkali metal salts produced in the first reaction step are soluble therein. The reactions are thus always carried out in homogeneous solutions. The yields of the ligand systems are generally not very high. In the case of silicon-bridged ligand systems, the best yields are achieved if a solution of the indenyl anion is added dropwise to a solution of the bisalkyldichlorosilane, which makes two reaction vessels necessary. This results in poor space-time yields. Since distillative purification of the products is not possible and recrystallization is unsuccessful in most cases, complex chromatographic purification of the products is almost always necessary. Moreover, the use of ethereal solvents and chromatographic purification steps and the low yields of the ligand systems are extremely prohibitive for an industrial process.

More specifically, the bridged metallocenes are prepared by deprotonation of the ligand systems using two equivalents of butyllithium and subsequent reaction with the metal tetrahalides or the THF adducts thereof. The solvents used are tetrahydrofuran or methylene chloride. However, methylene chloride can only be employed at very low temperatures (−78° C.). These solvents are used since the ligand systems and the dilithio salts formed after the deprotonation are very readily soluble therein. The reactions are thus always carried out in homogeneous solutions. Only the metal tetrahalides can be in suspended form, depending on the amount of solvent and the temperature. In principle, three different preparation processes are used in the prior art for bridged metallocenes of the bisindenyl type:

Method A

The ligand system is dissolved in tetrahydrofuran and converted to the dilithio salt using two equivalents of butyllithium. The solution of this salt is added dropwise to a solution of metal tetrahalide or the THF adduct thereof in tetrahydrofuran. When the reaction is complete, the solvent is stripped off and the desired racemate of the metallocene is separated from the meso form and impurities and isolated by extraction and crystallization using various solvents.

This method has the disadvantage that two reaction vessels are necessary. In addition, the use of large amounts of tetrahydrofuran causes problems on an industrial scale. The metal tetrahalides, such as, for example, $ZrCl_4$, must be introduced into the solvent at −78° C. since at higher temperatures they react with the solvent very vigorously and with partial decomposition, which is extremely prohibitive for an industrial process. The THF adducts of the metal tetrahalides, such as, for example, $ZrCl_4 \cdot 2THF$, which are easier to handle, are not commercially available. The preparation of the THF adducts is complex (Inorg. Synth. 21 (1982) 135).

Method B

The dilithio salt of the ligand system is prepared as described under A in tetrahydrofuran or diethyl ether and isolated as a solid by removal of the solvent and slow drying in a high vacuum. The extremely air-sensitive and partially pyrophoric salt is introduced at −78° C. into a suspension of the metal tetrahalide, such as, for example, $ZrCl_4$, in methylene chloride. At higher temperatures, explosive reactions between the dilithio salt and methylene chloride can occur. When the reaction is complete at room temperature, the desired racemate of the metallocene is separated from the meso form and various impurities and isolated by extraction and crystallization using various solvents.

This method has the disadvantage that it is carried out in two steps with isolation and complex drying of the intermediates. Handling of the extremely air-sensitive dilithio salt causes considerable problems on an industrial scale and in addition is hazardous due to the spontaneous combustion in air. The necessity for very low reaction temperatures of −78° C. and the use of the methylene chloride, which is difficult to dispose of, is again extremely prohibitive for an industrial process.

Method C

A solution, prepared as under A, of the dilithio salt in tetrahydrofuran and a solution of the metal tetrahalide (employed as the THF adduct) in tetrahydrofuran are slowly and simultaneously, introduced dropwise into a reaction vessel already containing solvent for dilution. When the reaction is complete, the desired racemate of the metallocene is separated from the meso form and various impurities are isolated by extraction and crystallization using various solvents.

This method has the disadvantage that very large volumes of solvent (which must be disposed of) and very long reaction times are necessary, which results in extremely poor space-time yields. In addition, the THF adduct of the metal tetrahalides is not commercially available.

All the preparation methods initially give the bridged bisindenylmetallocenes in two isomeric forms, a racemic form and a meso form. Depending on the reaction temperature and the type of ligand system, the ratio between these isomeric forms can vary within a certain range, but is generally in the region of 1:1. However, if the metallocenes are used as catalysts for the stereospecific polymerization of olefins, such as, for example, in the industrially important preparation of isotactic polypropylene, the meso form must be removed quantitatively since it polymerizes nonspecifically. According to the prior art, the separation of the isomeric forms and the isolation of the pure racemate are carried out by complex extraction methods or recrystallization in diverse solvents and in some cases are only incomplete. In addition to high preparative costs and the use of large amounts of solvent, these processes also result in very large material losses. Both are prohibitive for an industrial process.

The object was thus to find a process which avoids the disadvantages known from the prior art in the preparation of the ligand systems, the synthesis of the metallocenes and the separation of the racemic meso forms.

Surprisingly, it has now been found that bridged ligand systems of the bisindenyl type of the formula III can be obtained in a very simple manner, with better space-time yields and using industrially unproblematic solvents, if the ligand systems are prepared by a heterogeneous reaction route in aliphatic or aromatic hydrocarbons in accordance with the reaction scheme below.

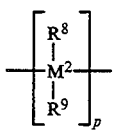

where $M^2$ is carbon, silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$haloaryl, $(C_2-C_{10})$alkynyl, $-SiR^7_3$ (with $R^7$ as defined above), halogen or heteroaromatic radicals having 5 or 6 ring members and optionally one or more hetero atoms, or together with the atoms connecting them, form one or more rings, and p is 1, 2 or 3, and X is a nucleophilic leaving group.

To this end, a solution or suspension of the appropriate indene of the formula I is deprotonated in a solvent or solvent mixture using butyllithium or another strong base, giving, when the reaction is complete, a suspension of the metallated product with the majority of the resultant salt in undissolved form. The solvent should be selected so that the salt is still significantly soluble. Examples of these solvents are aliphatic or aromatic solvents, such as pentane, hexane, isohexane, toluene or xylene, to which small amounts of ethereal solvents, such as diethyl ether, diisopropyl ether or tetrahydrofuran, can be added in order to increase the reactivity and to adjust the solubility in an optimum manner. The appropriate reagent of the formula II can then be added directly to this suspension in order to introduce the bridge function and brought to reaction.

When the reaction is complete, the reaction mixture can be worked up in a conventional manner. A reaction

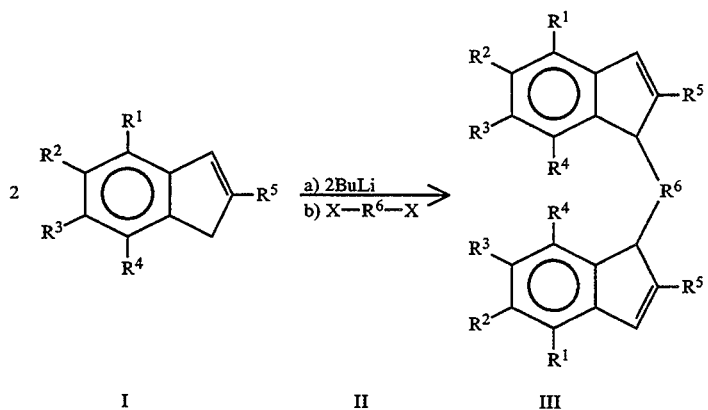

I                II              III whereby $R^1$, $R^2$, $R^3$, $R^4$ and $R^5$ are identical or different and are hydrogen, $(C_1-C_{20})$alkyl, $(C_6-C_4)$aryl, $(C_1-C_{10})$alkenyl, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$haloaryl, $(C_2-C_{10})$alkynyl, $-SiR^7_3$ where $R^7$ is $(C_1-C_{10})$alkyl, halogen or heteroaromatic radicals having 5 or 6 ring members and optionally one or more hetero atoms, or adjacent radicals $R^1-R^4$, together with the atoms connecting them, form one or more rings, route of this type results in a considerable increase in the yield of ligand systems of the formula III. In addition, it is a one-pot process which is very simple to carry out industrially, uses solvents which can readily be used industrially and in addition requires only small amounts of solvent. The space-time yields are significantly higher than those of the prior art. Complex purification and separation operations of the ligand systems are unnecessary.

Surprisingly, it has likewise been found that the bridged metallocenes of the formula IV are obtained in relatively high yields in a technically very simple process if the synthesis of the metallocene is carried out in a heterogeneous reaction in accordance with the reaction scheme below.

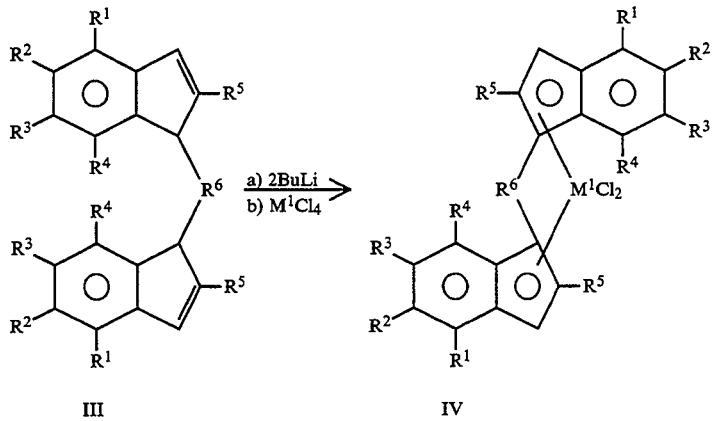

III    IV whereby $M^1$ is a metal from the group consisting of titanium, zirconium, hafnium, vanadium, niobium and tantalum, $R^1$, $R^2$, $R^3$, $R^4$ and $R^5$ are identical or different and are hydrogen, $(C_1-C_{20})$alkyl, $C_6-C_{14}$)aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$haloaryl, $(C_2-C_{10})$alkynyl, $-SiR^7_3$ where $R^7$ is $(C_1-C_{10})$alkyl, halogen or heteroaromatic radicals having 5 or 6 ring members and optionally one or more hetero atoms, or adjacent radicals $R^1-R^4$, together with the atoms connecting them, form one or more rings,

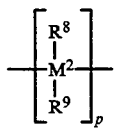

where $M^2$ is carbon, silicon, germanium or tin, and $R^8$ and $R^9$ are identical or different and are hydrogen, $(C_1-C_{20})$alkyl, $C_6-C_{14}$)aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$haloaryl, $(C_2-C_{10})$alkynyl, $-SiR^7_3$ (with $R^7$ as defined above), halogen or hereroaromatic radicals having 5 or 6 ring members and optionally one or more hetero atoms, or together with the atoms connecting them, form one or more rings, and p is 1, 2 or 3.

By using this process to prepare metalocenes of the formula IV, the disadvantages known from the prior art are avoided, and very simple separation of the racemic and meso forms is possible. In the novel process, a solution or suspension of the appropriate ligand system of the formula III is deprotonated in a solvent or solvent mixture using butyllithium or another strong base to give the dianion, giving a suspension of metallated product with the majority of the resultant salt in undissolved form. The solvent should be selected so that the salt is still significantly soluble. Examples of these solvents are aliphatic or aromatic solvents, such as pentane, hexane, isohexane, toluene or xylene, to which small amounts of ethereal solvents, such as diethyl ether, diisopropyl ether or tetrahydrofuran, can be added in order increase the reactivity and to adjust the solubility in an optimum manner. The commercially available metal tetrahalide, such as, for example, $ZrCl_4$, is then added to this suspension and brought to reaction.

The solvent or solvent mixture is selected so that, when the reaction is complete, only the desired racemate of the metallocene IV, but not the meso form, is in suspension. The desired racemic form can thus be filtered off directly from the reaction mixture. Formation of the solvent mixture in a suitable manner can also be delayed until the reaction has been terminated, for example by addition of THF to the toluene reaction batch. By using solvent mixtures comprising aliphatic or aromatic hydrocarbons and ethereal components, such as, for example, toluene/tetrahydrofuran, toluene/diethyl ether, xylene/tetrahydrofuran, hexane/tetrahydrofuran or isohexane/tetrahydrofuran mixtures, a mixture can be produced for virtually any metallocene of the formula IV, enabling separation of the two isomeric forms in this way. The addition of an ethereal component, such as diethyl ether or tetrahydrofuran, furthermore has the advantage that the metal tetrahalide is dissolved through the formation of adducts and thus unreacted metal tetrahalide does not occur as an impurity in the precipitated product. Only the racemate precipitated when the reaction is complete is contaminated by lithium chloride formed, which is sparingly soluble in solvents of this type. However, this contamination is unimportant if the metallocene is used as a catalyst component for the polymerization of olefins since it has no adverse effects.

This novel method is thus a one-pot process which is simple to carry out industrially, giving the pure racemic form, starting from commercially available starting materials. Space-time yields are significantly higher than those of the processes hitherto. The disadvantage known from the prior art are avoided.

The invention thus relates to a process for the preparation of bridged ligand systems of the formula III and to a process for the preparation of metallocenes of the formula IV in which $M^1$ is a metal from the group consisting of titanium, zirconium, hafnium, vanadium, niobium and tantalum, $R^1$, $R^2$, $R^3$, $R^4$ and $R^5$ are identical or different and are hydrogen, $(C_1-C_{20})$alkyl, $(C_6C_{14})$aryl, $(C_1-C_{10})$alkoxy, $(C_2-C_{10})$alkenyl, $(C_7-C_{20})$arylalkyl, $(C_7C_{20})$alkylaryl, $(C_6-C_{10})$aryloxy, $(C_1-C_{10})$fluoroalkyl, $(C_6-C_{10})$haloaryl, $(C_2-C_{10})$alkynyl, —SIR$^7_3$ where R$^7$ is (C$_1$–C$_{10}$)alkyl, halogen or heteroaromatic radicals having 5 or 6 ring members and optionally one or more hetero atoms, or adjacent radicals R$^1$–R$^4$, together with the atoms connecting them, form one or more rings, R$^6$ is

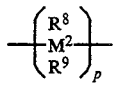

where M$^2$ is carbon, silicon, germanium or thin,

R$^8$ and R$^9$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$)fluoroalkyl, (C$_6$–C$_{10}$)haloaryl, (C$_2$–C$_{10}$)alkynyl, —SiR$^7_3$ (with R$^7$ as defined above), halogen or heteroaromatic radicals having 5 or 6 ring members and optionally one or more hetero atoms, or, together with the atoms connecting them, form one or more rings, and p is 1, 2 or 3, and X is a nucleophilic leaving group, such as, for example, halogen or tosylate, which comprises deprotonating the indenes of the formula I using strong bases in specific solvents or solvent mixtures, giving a suspension of the metallated product. The latter is reacted with the bridging reagent of the formula II, which can be added directly to the suspension. The ligand systems of the formula III are formed in very high yield. The ligand systems of the formula III are deprotonated in a specific solvent or solvent mixture using strong bases to give the dianion, giving the resultant metallated product as a suspension. The latter is reacted with the metal tetrahalide M$^1$Cl$_4$. The solvent or solvent mixture is selected so that, when the reaction is complete, only the desired racemate of the metallocene IV, but not the meso form, is in suspension, and the desired racemate can thus be filtered off directly from the reaction mixture. Formation of the solvent mixture in a suitable manner can also be delayed until the reaction has been terminated, for example by addition of THF to the toluene reaction batch.

In this description, alkyl represents straight-chain or branched alkyl. Halogen denotes fluorine, chlorine, bromine or iodine, in particular fluorine or chlorine. Examples of heteroaromatic radicals are thienyl, furyl and pyridyl.

In the formulae I to VI, it is preferred that M$^1$ is titanium, zirconium or hafnium, R$^1$, R$^2$, R$^3$, and R$^4$ are identical or different and are hydrogen, (C$_1$–C$_{10}$)alkyl, (C$_1$–C$_4$)alkoxy, (C$_2$–C$_6$)alkenyl, (C$_1$–C$_6$)fluoroalkyl or halogen, or the radicals R$^1$ and R$^2$, R$^2$ and R$^3$ or R$^3$ and R$^4$, together with the atoms connecting them, form one or more 4-, 5- or 6-membered rings, and R$^5$ is (C$_1$–C$_{10}$)alkyl, M$^2$ is carbon or silicon, R$^8$ and R$^9$ are identical or different and are hydrogen, (C$_1$–C$_{10}$)alkyl, (C$_6$–C$_{14}$)aryl, (C$_1$–C$_4$)alkoxy, (C$_2$–C$_6$)alkenyl, (C$_1$–C$_6$)fluoroalkyl or halogen, or, together with the atoms connecting them, form a 5- or 6-membered ring, is 1 or 2 and X is halogen. In particular, M$^1$ is zirconium, R$^1$, R$^2$, R$^3$ and R$^4$ are identical or different and are hydrogen or (C$_1$–C$_{10}$)alkyl, the radicals R$^1$ and R$^2$, together with the atoms connecting them, form a 6-membered aromatic ring, R$^5$ is methyl, M$^2$ is silicon, R$^8$ and R$^9$ are methyl or phenyl, p is 1, and x is chlorine, The indene derivatives of formula I serving as starting materials are commercially available or can be prepared by methods known from the literature (Bull. Soc. Chim. Fr. 11 (1973) 3092; Bull. Soc. Chim. Fr. 3 (1967) 987; J. Org. Chem. 55 (1990) 247).

They can be prepared from the corresponding indanones by reduction and elimination of water (Bull. Soc. Chim. Fr. 11 (1973) 3092).

The indanones can be prepared by processes known from the literature (J. Org. Chem. 46 (1981) 3758; J. Org. Chem. 23 (1958) 1441, Eur. J. Med. Chem. 25 (1990) 603, Chem. Lett. 5 (1988) 901; Ann. Chem. 11 (1985) 2116; EP 0 421 759; EP 0 162 465; J. Med. Chem. 25 (1990) 765, Organomet. Chem. 7 (1988) 936; Tetrahedron Lett. 29 (1988) 2183; J. Am. Chem. Soc. 72 (1950) 3286; Zh. Org. Khim. 12 (1976) 1502).

Some specific substituted indanones of the formula VIIa/b can be prepared by reaction of aromatic compounds of the formula V with a propionic acid derivative of the formula VI in the presence of a Friedel-Crafts catalyst, such as, for example, AlCl$_3$ in accordance with the reaction scheme below

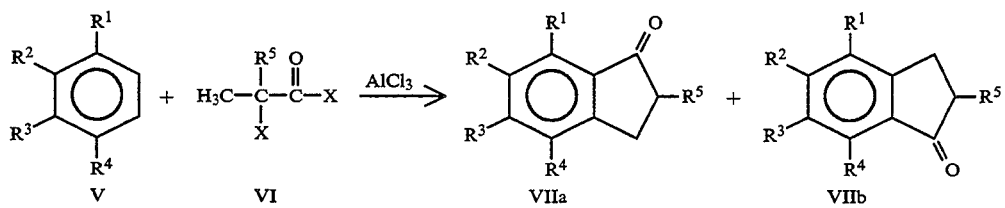

whereby R$^1$–R$^5$ have the same meaning as for figure I.

The indenes of the formula I are deprotonated in a solvent or solvent mixture using a strong base. Suitable bases are butyllithium, sodium hydride, sodium amide, potassium hydride, hexyllithium, methyllithium or elemental sodium or potassium. Preference is given to butyllithium.

The composition and amount of the solvent or solvent mixture are selected so that, when the reaction is complete, the metallated product is in the form of a suspension and the majority of the salt produced is in undissolved form. The solvent should be selected so that the salt is still significantly soluble. Examples of such solvents are aliphatic or aromatic solvents, such as pentane, hexane, isohexane, toluene and xylene, to which small amounts of ethereal solvents, such as diethyl ether, tetrahydrofuran or diisopropyl ether, can be added in order to increase the reactivity and to adjust the solubility in an optimum manner. Preferred solvents are toluene, toluene/diethyl ether, toluene/tetrahydrofuran, hexane/tetrahydrofuran or isohexane/tetrahydrofuran.

The reaction can be carried out at from −78° C. to 150° C., preferably at from 0° C. to 120° C.

The molar ratio between the reactants is in the range from 1:0.8–1.2, preferably 1:1.

The appropriate reagent of the formula II is added directly to this suspension and is reacted in order to introduce the bridged function.

The reaction can be carried out at from −50° C. to 150° C., preferably at from 20° C. to 120° C.

The molar ration between the metallated indenes I and II is from 1:0.3–0.7, preferably 1:0.5.

When the reaction is complete, the reaction mixture can be worked up in a conventional manner, by hydrolysis and extraction of the organic products and subsequent purification by distillation, chromatography or crystallization or by removal of the inorganic components by filtration and purification of each soluble organic product. In many cases, the ligand systems of the formula III are formed in such high yield that further purification is unnecessary. The reaction batches can then be employed directly for further reaction to give the metallocene.

The ligand systems of the formula III are deprotonated in a solvent or solvent mixture using a strong base. Suitable bases are butyllithium, sodium hydride, sodium amide, potassium hydride, hexyllithium, methyllithium or elemental sodium or potassium. Preference is given to butyllithium. The composition and amount of the solvent or solvent mixture is selected so that, when the reaction is complete, the resultant metallated ligand system ill is in the form of a suspension. The resultant dianion is subsequently reacted with the metal tetrahalide $M^1Cl_4$, it being possible to add the metal tetrahalide directly to the suspension.

The composition and amount of the solvent or solvent mixture is selected so that, when the reaction is complete, the resultant metallocene IV is in the form of a suspension. The solvent should be selected so that only the resultant racemic form, but not the meso form, is in undissolved form. Examples of suitable solvents are aliphatic or aromatic solvents, such as pentane, hexane, isohexane, toluene and xylene, to which small amounts of ethereal solvents, such as diethyl ether, tetrahydrofuran or diisopropyl ether, can be added in order to increase the reactivity and to adjust the solubility in an optimum manner. If ethereal components are used, such as, for example, if THF is added, unreacted metal tetrahalide and diverse reaction products are also kept in solution and thus separated from the racemate. Formation of the solvent mixture in a suitable manner can also be delayed until the reaction is terminated, for example by the addition of THF to the toluene reaction batch. Preferred solvents are toluene, toluene/tetrahydrofuran, toluene/diethyl ether, hexane/tetrahydrofuran or isohexane/tetrahydrofuran.

The reaction can be carried out at from −78° C. to 100° C., preferably at from −40° C. to 80° C.

The molar ratio between the reactants III and $M^1Cl_4$ is in the range from 1:0.8–3, preferably from 1:1–1.5.

The racemic form of the metallocene IV is filtered off directly when the reaction is complete. If complete separation from the meso form or other interfering impurities is not achieved in this process, subsequent purification by extraction or recrystallization can also be carried out. Suitable solvents for this purpose are all aliphatic or aromatic solvents, ethereal solvents, such as diethyl ether or THF, or halogenated hydrocarbons, such as chloroform or methylene chloride.

rac/meso mixtures can very advantageously be separated by stirring with small amounts of tetrahydrofuran or halogenated hydrocarbons, such as methylene chloride or chloroform. During this operation, the racemate remains as a residue, which can be filtered off.

The process according to the invention for the preparation of the ligand systems III has the advantage that it is a one-pot process which is very simple to carry out industrially, uses solvents which can readily be employed industrially and in addition only requires small amounts of solvent. The yields of III and the space-time yields are significantly higher than those of the prior art. Complex purification and separation operations for the ligand systems III are unnecessary.

The process according to the invention for the preparation of the metallocenes IV in the racemic form has the advantage that it is a one-pot process which is simple to carry out industrially starting from commercially available starting materials. The space-time yields are significantly higher than those of the processes hitherto. The disadvantages known from the prior art for the preparation of metallocenes and isolation of the racemic form are avoided. For these reasons, the bisindenyl type metallocene catalysts of the formula IV, which are prepared in accordance with the process of this invention, are suitable for the preparation of isotactic polyolefins, polyolefin waxes and copolymers.

The examples below are intended to illustrate the invention in greater detail.

All the working operations below were carried out under an Ar atmosphere (Schlenk technique) unless otherwise stated.

EXAMPLES

Ligand Systems:

Example A (Heterogeneous Reaction Method)

Dimethylbisindenylsilane (1 )

Technical-grade indene (90%) was first filtered through aluminum oxide (superactive) for crude purification and drying. 160 ml (400 mmol) of a 2.5M butyllithium solution in hexane were added at room temperature to a solution of 57 ml (446 mmol) of the indene (91–92%) in a solvent mixture comprising 430 ml of toluene and 32 ml of THF, and the mixture was refluxed for 1 hour. The mixture was cooled to room temperature, and 24.2 ml (200 mmol) of dimethyldichlorosilane were added to the orange suspension. The mixture was refluxed for 5 hours and subsequently poured into water. The mixture was extracted several times with ethyl acetate. The combined organic phases were dried over sodium sulfate and freed from solvent under reduced pressure. The residue which remained was dried for several hours in an oil-pump vacuum at 50° C. 56 g (97%) of the ligand system 1 were obtained as a brownish oil (isomer mixture, 2 diastereomers, 1 double-bond isomer). The isomer mixture can be used directly for the preparation of the metallocene.

Comparative Example A (homogeneous Reaction Method)

Technical-grade indene (90%) was first filtered through aluminum oxide (superactive) for crude purification and drying. 160 ml (400 mmol) of a 2.5M butyllithium solution in hexane were added at room temperature to a solution of 57 ml (446 mmol) of the indene (91–92%) in 300 ml of diethyl ether, and the mixture was refluxed for 1 hour. The mixture was cooled to room temperature, and 24.2 ml (200 mmol) of dimethyldichlorosilane were added to the orange solution. The solution was refluxed for 5 hours and subsequently poured into water. The mixture was extracted several times with ethyl acetate. The combined organic phases were dried over sodium sulfate and freed from solvent under reduced pressure. The residue which remained was dried for several hours in an oil-pump vacuum at 50° C. and subsequently chromatographed on silica gel 60. 9.8 g (17%) of the ligand system 1 (isomer mixture, 2 diastereomers) were eluted using an eluent mixture of hexane/methylene chloride (5:1 ).

Comparative Example A (Homogeneous Reaction Method, Inverse Addition)

Technical-grade indene (90%) was first filtered through aluminum oxide (superactive) for crude purification and drying. 160 ml (400 mmol) of a 2.5M butyllithium solution in hexane were added at room temperature to a solution of 57 ml (446 mmol) of the indene (91–92%) in 200 ml of diethyl ether, and the mixture was refluxed for 1 hour. The mixture was coiled to room temperature, and the orange solution was added dropwise over the course of 2 hours to a solution of 24.2 ml (200 mmol) of dimethyldichlorosilane in 100 ml of diethyl ether. The solution was refluxed for 5 hours and subsequently poured into 25 water. The mixture was extracted several times with ethyl acetate. The combined organic phases were dried over sodium sulfate and freed from solvent under reduced pressure. The residue which remained was dried for several hours in an oil-pump vacuum at 50° C. and subsequently chromatographed on silica gel 60. 39 g (67%) of the ligand system 1 (isomer mixture, 2 diastereomers) were eluted using an eluent mixture of hexane/methylene chloride (5:1).

Example B (Heterogeneous Reaction Method)

Dimethylbis (4,5-benzo-2-methylindenyl)silane (2)

290 ml (724 mmol) of a 2.5M butyllithium solution in hexane were added at room temperature to a solution of 130 g (725 mmol) of an isomer mixture of 4,5-benzo-2-methylindene and 6,7-benzo-2-methylindene (3:2) in a solvent mixture comprising 1600 ml of toluene and 60 ml of THF and the mixture was refluxed for 1 hour. The mixture was cooled to room temperature, and 44 ml (362 mmol) of dimethyldichlorosilane were added to the pale brown suspension. The mixture was refluxed for 5 hours and poured into water. The mixture was extracted several times with ethyl acetate. The combined organic phases were washed with water and subsequently dried over sodium sulfate. The solvent was removed under reduced pressure and the residue was dried for several hours in an oil-pump vacuum at 50° C. The solid residue was stirred with 150 ml of hexane and filtered. The solid which remained was then washed with 100 ml of hexane and dried in an oil-pump vacuum. 85 g (57%) of the ligand system 2 were obtained as a white powder (2 diastereomers).

The hexane filtrate contains both starting material and product. Chromatography on silica gel 60 using an eluent mixture of hexane/ethyl acetate (20:1) eluted successively 16 g of unreacted starting material and a further 25 g of ligand system. 2. The total yield of ligand system 2 is thus 110 g (73% with respect to Si and 83% with respect to reacted starting material).

Comparative Example B (Homogeneous Reaction Method, Inverse Addition)

290 ml (724 mmol) of 2.5M butyllithium solution in hexane were added at room temperature to a solution of 130 g (725 mmol) of an isomer mixture of 4,5-benzo-2-methylindene and 6,7-benzo-2-methylindene (3:2) in 800 ml of THF, and the mixture was refluxed for 1 hour. The mixture was cooled to room temperature, and the dark-red solution was added dropwise over the course of 2 hours to a solution of 44 ml (362 mmol) of dimethyldichlorosilane in 300 ml of THF. The solution was refluxed for 5 hours and poured into water. The mixture was extracted several times with ethyl acetate. The combined organic phases were washed with water and subsequently dried over sodium sulfate. The solvent was removed under reduced pressure, and the residue was dried for several hours in an oil-pump vacuum at 50° C. The residue was chromatographed on silica gel 60. 20 g of unreacted starting material and further 52 g of ligand system 2 were eluted using an eluent mixture of hexane/ethyl acetate (20:1 ). The yield was 34% with respect to Si and 41% with respect to reacted starting material.

Metallocene Syntheses:

Example C rac-Dimethylsilanediylbisindenylzirconium dichloride (3)

14.6 ml (36.5 mmol) of a 2.5M butyllithium solution in hexane were added at room temperature to a solution of 5.0 g (17.3 mmol) of the ligand system 1 in 100 ml of toluene and 5 ml of diethyl ether, and the mixture was refluxed for 3 hours. 4.04 g (17 mmol) of zirconium tetrachloride were added at −20° C. to the ochre suspension. The mixture was slowly warmed to room temperature and then heated at 80° C. for 1 hour. The mixture was cooled to room temperature, and the yellow precipitate was filtered off from the dark red-brown reaction solution and washed with 25 ml of toluene. 6.4 g of the racemate 3 were obtained as a yellow powder (also containing about 1.5 g of LiCl, pure yield 65%).

The LiCl-free complex can be isolated by extraction of the residue by a total of 170 ml of methylene chloride.

Evaporation of the filtrate gives 4.3 g (57%) of the pure racemate 3 as a yellow-orange crystal powder.

Example D

Dimethylsilanediylbis(4,5-benzo-2-methylindenyl)-zirconiumdichloride (4)

111 ml (282 mmol) of a 2.5M butyllithium solution in hexane were added at room temperature to a solution of 55.0 g (132 mmol) of the ligand system 2 in 1000 ml of toluene, and the mixture was refluxed for 4 hours. 33.8 g (145 mmol) of zirconium tetrachloride were added at −20° C. with vigorous stirring to the resultant pale yellow suspension. The mixture was warmed to room temperature over the course of 1–2 hours and stirred at this temperature for a further 1–2 hours (a small sample was taken for NMR analysis; according to the NMR spectrum, the racemic and meso forms are present in a ratio of from 1:1–1.5). The yellow suspension was cooled to 0° C., and 300 ml of tetrahydrofuran were added over the course of 30 minutes. The mixture was stirred for 5-10 minutes, and the dark suspension was filtered through a G3 frit. The yellow residue was washed with THF and dried in an oil-pump vacuum. 57 g of the metallocene 4 were obtained as a mixture of racemate and the meso form in a ratio of 3:1 in the form of a yellow crystal powder (also containing about 10 g of LiCl). The theoretical pure yield of rac/meso-4 is 61% and that of rac-4 is 46%.

It was possible to isolate the pure racemate 4 by extraction of the crude product by tetrahydrofuran and methylene chloride, the racemate remaining as a yellow crystal powder, and the meso form and LiCl components being washed out. To this end, the 57 g of the metallocene mixture (rac/meso 3:1) were first stirred with 200 ml of tetrahydrofuran and filtered. The yellow residue which remained was subsequently stirred and filtered twice with 100 ml of methylene chloride in each case. 27 g of the pure racemate 4 were obtained. The yield was 35%.

(The pure meso form could be isolated by evaporating the THF and methylene chloride extracts to a small volume and crystallizing at $-35°$ C.).

Example E

Dimethylsilanediylbisindenylzirconium dichloride (3), rac/meso separation

The metallocene was prepared by Method B:

16.2 g (53.7 mmol) of thoroughly dried $Li_2(Me_2Silnd_2)$ (prepared from ligand system 1 and butyllithium in diethyl ether) were added at $-78°$ C. to a suspension of 12.5 g (53.7 mmol) of zirconium tetrachloride in 200 ml of methylene chloride. The mixture was warmed to room temperature overnight. The solvent was stripped off and the residue was dried in an oil-pump vacuum, giving an orange powder. This contained the metallocene 3 as a mixture of the racemic and meso forms in the ration 2:1, small amounts of unreacted zirconium tetrachloride, lithium chloride and small amounts of decomposition products. 30 ml of tetrahydrofuran were added to the orange powder at 0° C. with vigorous stirring, and the mixture was stirred at room temperature for 2 hours. The dark suspension was filtered through a G3 frit. The orange residue was washed with 20 ml of tetrahydrofuran and dried in an oil-pump vacuum. 15.7 g (65%) of the pure racemate 3 were obtained in the form of an orange crystal powder.

We claim:

1. A process for the preparation of a compound of the formula III

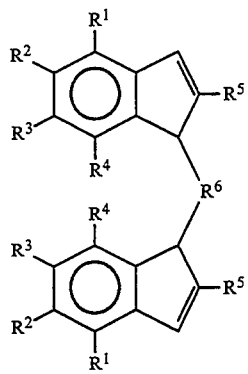

(III)

comprising, deprotonating a solution or suspension of an indene of the formula I

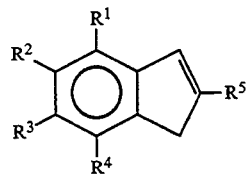

(I)

in a solvent mixture containing a base to give a suspension of a metallated product of the compound of formula I, adding to the suspension of the metallated product a compound of the formula II

  X—R$^6$—X  (II)

and reacting the suspension of the metallated product and compound of the formula II, whereby for the formulae I-III,
$R^1$, $R^2$, $R^3$, $R^4$ and $R^5$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$alkyaryl, $(C_7-C_{20})$alkylaryl, $(C_6-C_{10})$ aryloxy, $(C_1-C_{10})$fluoroalkyl, $(C_6-C_{10})$haloaryl, $(C_2-C_{10})$alkylnyl, —SiR$^7$$_3$ where R$^7$ is $(C_1-C_{10})$alkyl, halogen or heteroaromatic radicals having 5 to 6 ring members and optionally one or more hetero atoms, or adjacent radicals $R^1$-$R^4$, together with the atoms connecting them, form one or more rings,

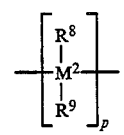

where M$^2$ is carbon, silicon, germanium or tin, R$^8$ and R$^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylakyl, $(C_7-C_{20})$alkylaryl, $C_6-C_{10})$aryloxy, $(C_1-C_{10})$fluoroalkyl, $(C_6-C_{10})$haloaryl, $(C_2-C_{10})$alkynyl, —SiR$^7$$_3$, halogen or heteroaromatic radicals having 5 to 6 ring members and optionally one or more hetero atoms, or together with the atoms connecting them, form one or more rings, and p is 1, 2 or 3, and X is a nucleophilic leaving group.

2. The process as claimed in claim 1, wherein the base is selected from the group consisting of butyllithium, sodium hydride, sodium amide, potassium hydride, hexyllithium, methyllithium or elemental sodium or potassium.

3. The process as claimed in claim 1, wherein the solvent mixture is an aliphatic or aromatic hydrocarbon solvent and an ethereal solvent.

4. The process as claimed in claim 3, wherein the ethereal solvent is selected from the group consisting of diethyl ether, tetrahydrofuran and diisopropyl ether.

5. The process as claimed in claim 3, wherein the aliphatic or aromatic hydrocarbon solvent is selected from the group consisting of pentane, hexane, isohexane, toluene and xylene.

* * * * *

UNITED STATES PATENT AND TRADEMARK OFFICE
CERTIFICATE OF CORRECTION

PATENT NO. : 5,391,790
DATED : February 21, 1995
INVENTOR(S) : Rohrmann et al.

It is certified that error appears in the above-indentified patent and that said Letters Patent is hereby corrected as shown below:

Column 3, line 61, "$(C_6-C_4)$aryl" should be -- $(C_6-C_{14})$aryl --.

Column 3, line 62, "alkenyl", first occurrence, should be -- alkoxy --.

Column 4, line 5, before the formula, insert -- $R^6$ is --.

Column 4, line 67, "metaliocenes" should be -- metallocenes --.

Column 5, formula IV should be :

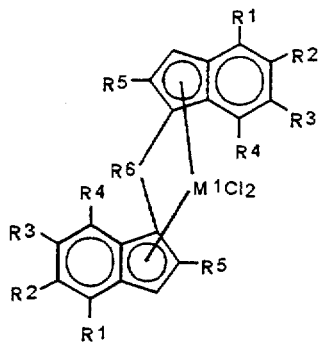

Column 5, line 39, before the formula, insert -- $R^6$ is --.

Column 5, line 54, "metaliocenes" should be -- metallocenes --.

Column 6, line 65, "$(C_6C_{14})$aryl" should be -- $(C_6-C_{14})$aryl --.

UNITED STATES PATENT AND TRADEMARK OFFICE
CERTIFICATE OF CORRECTION

PATENT NO. : 5,391,790
DATED : February 21, 1995
INVENTOR(S) : Rohrmann et al.

It is certified that error appears in the above-indentified patent and that said Letters Patent is hereby corrected as shown below:

Column 6, line 66, "$(C_2-C_{10})$alkenyl" should be -- $(C_2-C_{10})$alkenyl --.

Column 6, line 67, "$(C_7C_{20})$alkylaryl" should be -- $(C_7-C_{20})$alkylaryl --.

Column 7, line 1, "$-SIR^7_3$" should be -- $-SiR^7_3$ --.

Column 8, line 7, before "is 1 or 2" insert -- p --.

Column 8, line 14, "," should be -- . --.

Column 8, line 52, "burtyllithium" should be -- butyllithium --.

Column 9, line 33: "ill" should be -- III --.

Column 11, lines 3-4, "dimethyldichiorosilane" should be -- dimethyldichlorosilane --.

Column 11, line 24, "coiled" should be -- cooled --.

Column 11, line 29, delete "25".

Claim 1, column 14, line 36, "$(C_7-C_{20})$alkyaryl" should be -- $(C_7-C_{20})$arylaklyl --.

Claim 1, column 14, line 38, "$(C_2-C_{10})$alkylnyl" should be -- $(C_2-C_{10})$alkynyl --.

Claim 1, column 14, line 40, "5 to 6" should be -- 5 or 6 --.

UNITED STATES PATENT AND TRADEMARK OFFICE
CERTIFICATE OF CORRECTION

PATENT NO. : 5,391,790
DATED : February 21, 1995
INVENTOR(S) : Rohrmann et al.

It is certified that error appears in the above-indentified patent and that said Letters Patent is hereby corrected as shown below:

Claim 1, column 14, line 45, before the formula, insert -- $R^6$ is --.

Claim 1, column 14, between lines 50–55, the line beginning with "gen or heteroaromatic . . .", "5 to 6" should be -- 5 or 6 --.

Signed and Sealed this

Twelfth Day of September, 1995

BRUCE LEHMAN

Attest:

Attesting Officer

Commissioner of Patents and Trademarks